Figure 4:
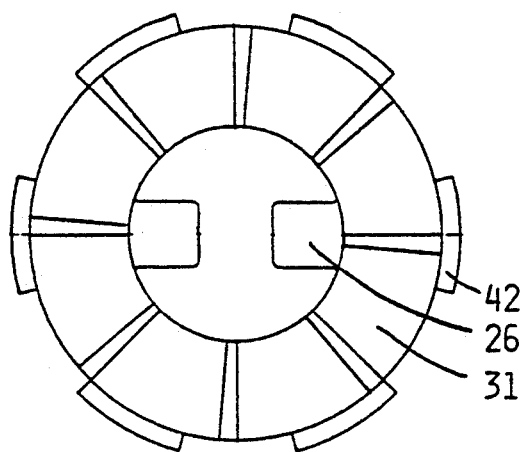

United States Patent [19]
Rex et al.

[11] Patent Number: 5,331,954
[45] Date of Patent: Jul. 26, 1994

[54] DEVICE FOR NASAL DELIVERY OF LIQUID MEDICATIONS

[75] Inventors: Jorn Rex, Roskilde; Kim Steengaard, Hvidovre; Svend Elk, Birkeroed, all of Denmark

[73] Assignee: Novo Nordisk A/S, Bagsvaerd, Denmark

[21] Appl. No.: 54,913

[22] Filed: Apr. 27, 1993

Related U.S. Application Data

[63] Continuation of Ser. No. 793,412, Jan. 13, 1992, abandoned.

[30] Foreign Application Priority Data

Dec. 21, 1990 [DK] Denmark ............................. 3028/90

[51] Int. Cl.$^5$ .................... A61M 15/08; A61M 11/00; A61M 5/00; A62B 7/00
[52] U.S. Cl. .......................... 128/200.22; 128/207.18; 128/200.14; 604/232; 604/211
[58] Field of Search ...................... 128/200.14, 200.18, 128/200.19, 200.22, 203.12, 203.19, 203.21, 203.22, 203.23, 207.18; 604/207–209, 211, 218, 232, 135

[56] References Cited

U.S. PATENT DOCUMENTS

| | | | |
|---|---|---|---|
| 4,405,308 | 9/1983 | Jessup | 128/200.22 |
| 4,413,760 | 11/1983 | Paton | 604/209 |
| 4,498,904 | 2/1985 | Turner et al. | 604/211 |
| 4,962,868 | 10/1990 | Borchard | 222/49 |
| 4,973,314 | 11/1990 | Holm et al. | 604/211 |
| 5,017,190 | 5/1991 | Simon et al. | 604/209 |
| 5,104,380 | 4/1992 | Holman et al. | 604/232 |
| 5,112,317 | 5/1992 | Michel | 604/232 |
| 5,114,406 | 5/1992 | Gabriel et al. | 604/232 |

FOREIGN PATENT DOCUMENTS

| | | |
|---|---|---|
| 0308100 | 3/1989 | European Pat. Off. . |
| WO91/15303 | 10/1991 | PCT Int'l Appl. . |
| 1379688 | 1/1975 | United Kingdom . |

*Primary Examiner*—Edgar S. Burr
*Assistant Examiner*—Kimberly L. Asher
*Attorney, Agent, or Firm*—Steve T. Zelson

[57] ABSTRACT

A pen shaped device for nasal administration of doses of a liquid medicine, comprising a first and a second housing element, the first housing element (1) comprising a cartridge for the medicine, this cartridge being at one end closed by a piston (21) and being at its other end closed by a valve (7,9), which may be opened to connect the cartridge to a spray nozzle (12). When the two housing elements are rotated relatively to each other, a nut member (27) is proportional to the rotation moved along a threaded piston rod (22) to compress a helical spring (32) to act via the nut element (27) and the piston rod (22) on the piston (21) to put the content of the cartridge under pressure, which pressure may be released by opening the valve (7,9) to lead the medicine in the cartridge to the nozzle (12).

16 Claims, 2 Drawing Sheets

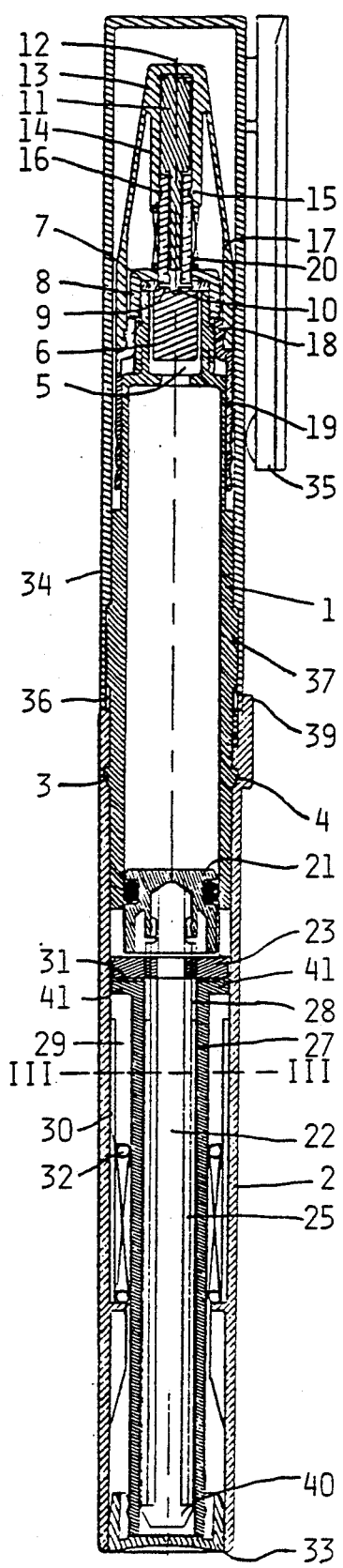
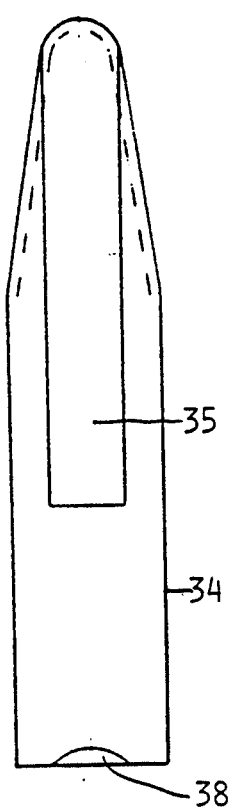
Fig. 2
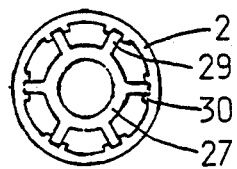
Fig. 3
Fig. 1

DEVICE FOR NASAL DELIVERY OF LIQUID MEDICATIONS

This application is a continuation application of co-pending application Ser. No. 07/793,412, filed Jan. 13, 1992, now abandoned.

The invention concerns a dispensing device for dispensing dosed quantities of a fluid medicine as an aerosol, e.g. insulin, to be assimilated through the nasal mucous membranes.

Many sorts of medicine are not appropriate for being orally consumed as they are destroyed very quickly in the alimentary canal. Such medicines, therefore, have to be injected to be directly assimilated in the blood.

When such medicines have to be taken frequently through a long period or even the life long as it is the case with, e.g. insulin for diabetics, the wish for a method of taking the medicines without frequent injections occurs. Here the assimilation through the nasal mucous membranes is seen as a solution.

From European Patent Application No. 308,100 is known a dispensing apparatus for dispensing metered quantities of pressurized fluid and in particular for nasal administration of insulin.

EP 308,100 meets the wishes for a device which may be used for nasal administration of e.g. insulin, as an activation of the device releases a metered quantity of liquid. However, the amount of liquid released by each activation is preset by the manufacturer of the spray valve, and if a bigger dose than this preset one is wanted, the device must be activated repetitively until the wanted dose is dispensed.

The use of a propellant gas as in EP 308,100 is undesirable for more reasons. First of all, precaution should be taken to assure that the propellant gas is kept out of contact with the medicine. Further, the content of sufficient propellant gas to dispense the total content of medicine involves the risk that an overdose is dispensed if the metering valve fails. Finally, as the device is intended to be disposed of when the medicine content is used up, it is against the current trend to use disposable devices containing propellant gases.

Consequently, it is the object of the invention to provide a dispensing apparatus for nasal administration of medicine such as insulin in preset doses without the use of a propellant gas. Another object is to provide a device which has the same neutral pen shape as the known pen syringes for subcutaneous injection of insulin.

This is obtained by a device for nasal administration of a number of measured doses of a liquid medicine, especially insulin, comprising a first and a second housing element coupled together to allow rotation but no axial displacement of the first housing element with respect to the second housing element, said first housing element comprising a cartridge containing the liquid and being sealed by a piston at the end coupled to the second housing element and being at its other end closed by a valve to communicate the liquid in the cartridge with a spray nozzle when opened, the device according to the invention being characterized in that it further comprises a threaded piston rod engaging the piston of the cartridge irrotational with respect to the first housing element and disposed in the second housing element to move axially therein, a nut element mounted irrotational but axially displacably in the second housing element and engaging the thread of the piston rod, a helical spring abutting at its one end an internal annular abutment on the second housing element and at its other end a shoulder on the nut element to press this nut element and thereby the piston rod and the piston in the directions towards the outlet end of the cartridge setting the liquid therein under pressure to be released by opening the valve for spraying out a dose of the liquid, the housing elements, the rod, and the nut cooperating so that relative rotation between the housing elements in a selected direction causes relative rotation between the rod and the nut element making the nut element move axially in the second housing element in a direction to compress the helical spring.

The device according to the invention further provides a dispenser which will work in all positions and in which the liquid remains sterile as no unclean air is to replace the liquid removed from the cartridge during the spraying.

According to the invention, the piston rod may be snap locked into the piston preventing a possible vacuum, which may emerge in the cartridge, from drawing the piston into the cartridge leaving an axial play between the piston rod and the piston.

To ensure that the liquid will hit the part of the nasal mucous membrane which is effective in assimilating the medicine, the nozzle is appropriately made to spray out the liquid at an angle of 0°-30° defining the spray as ranging from a jet spray to a fan shaped spray.

The nut element may define at least one radially protruding axially extending projection on an exterior portion thereof, and this projection or these projections may be received in one or more corresponding axially extending groove or grooves in an inner portion of the second housing element thereby providing a coupling between this housing element and the nut element ensuring that the nut element may be rotated with the second housing element and be axially displaced in this housing element.

A stop may be provided limiting the axial movement of the nut element into the second housing element, thus limiting the loading of the device to a set maximum dose.

Also the movement of the nut element along the piston rod may be limited to avoid setting a larger dose than actually remains in the cartridge.

In a preferred embodiment of the invention, the device has a removable protective cap configured to receive the first housing element and abutting when mounted there on the second housing element; and means for releasably coupling the protective cap and the first housing element for rotation together, so that rotation of the protective cap with respect to the second housing element causes rotation of the first housing element with respect to the second housing element.

The abutting edges of the second housing element and the protective cap may comprise pointing means and scale means, respectively, to measure the relative rotation of the protective cap, and thereby the first housing element, with respect to the second housing element. The displacement of the nut element is proportional to this relative rotation and the measuring of the relative rotation consequently is a measuring of the set dose.

Means may be provided for providing detents at selected rotational positions of the first housing element with respect to the second housing element making the extend of the relative rotation hearable, tactile, and visible as a click is heard and a resistance variation is felt each time a detent is passed during the relative rotation the size of which may be seen from the relative position of the pointing means and the scale.

The coupling means for coupling the protective cap to the first housing element may allow the protective cap to receive the first housing element in multiple different angular positions of the protective cap with respect to the first housing element to allow the protective cap to be oriented at a selected position with respect to the second housing element, regardless of the detent rotational position of the first housing element in the second housing element. This way it is always possible to mount the protective cap in position with the "O" of its scale in line with the pointing means on the second housing element.

By the abutting edges having interlocking means for defining a selected angular position of the protective cap with respect to the second housing element it may be ensured that the cap is mounted in its O-position when the pen is stored away after use. The interlocking means may appropriately comprise a recess on the abutting edge of the protective cap and a projection on the abutting edge of the second housing element, the projection being shaped to fit into the recess to define the selected position.

In a preferred embodiment of the device according to the invention, the piston rod is made irrotational by fitting through an opening in an anti-rotation disc, the opening being circular with at least one projection protruding into the opening, by the piston rod having a corresponding profile with recesses corresponding to the projections, and by the anti-rotary disc being at its periphery provided with alternating spaces and teeth fitting into a castellated end of the first housing element. Further, the anti-rotary disc serves as an abutment for the nut element limiting the movement of this element towards the cartridge.

The abutting faces of the nut element and the anti-rotary disc are shaped as annular ramps which when in mutual abutment allow only relative rotation of the first and second housing elements in a device loading direction. Thereby it is precluded that a relative rotation in a direction to unload the device to annul a set dose is continued when the device is unloaded. Such a continued relative rotation could draw the piston rod free of the piston and provide an axial play which would undermine the correct dosing.

In a preferred embodiment, the nut element may have a tubular extension coaxially surrounding the piston rod and terminated by a knob at the outer end of the second housing element, this knob being flush with the edge of this outer end, when the annular ramps of the anti-rotary disc and the nut member are in a mutual abutment giving a tactile and visible indication whether the device is loaded or not.

Figure 5:
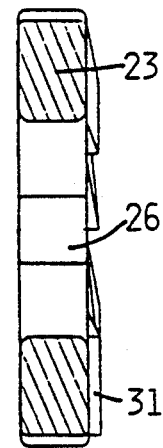

In the following the invention is specified in further detail with reference to the drawing in which FIG. 1 shows a plan view of a dispenser according to the invention, FIG. 2 shows a plan view of the protective cap, FIG. 3 shows a sectional view along the line III—III in FIG. 1, but without the piston rod, FIG. 4 shows an enlarged plan view of the anti-rotary disc, FIG. 5 shows a side view of the disc in FIG. 4.

Figure 6:
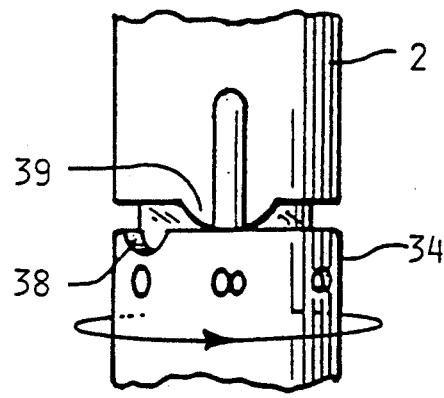
Figure 7:
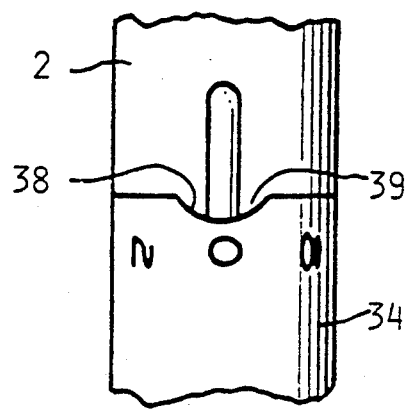

FIG. 6 shows an enlarged detail of the abutting edges of the protective cap and the second housing element in dose setting position, and FIG. 7 shows the detail of FIG. 6 in closed position for storing.

FIG. 1 shows a pen shaped device having a first housing element 1 and a second housing element 2 snapped together by an external bead 3, and the first housing element 1 being snapped into an annular groove 4 in the second housing element 2 permitting the two housing elements to be rotated in relation to each other about the common length axis, but not to be displaced in relation to each other along this axis.

The first housing element 1 forms a cartridge for a liquid medicine and is at its one end provided with a neck forming a valve chamber 5 communicating at its one end with the housing element and being at its other end closed by a valve block 6 fitting into an annular sealing 7 fitted to the valve chamber 5 by a ferrule 8. The valve block has radial ducts 9 leading to a central bore 10 and being at the outer ends sealed by the inner cylindric surface of the annular sealing 7 when the valve is closed. An inner element 11 of a spray nozzle has a rod fitting into the bore 10 with a small clearance leaving a duct leading to a spray nozzle 12 in a nozzle element 13 surrounding the inner element 11 leaving a fine duct from the bore 10 to the nozzle 12.

The nozzle element 13 is provided with a tubular central part 14 fitting over the part with the bore 10. An internal annular bead 15 in the part 14 is lodged in an annular groove 16 in the part with the central bore.

The nozzle element 13 further comprises a shirt 17 surrounding at some distance the tubular central part 14 and being at its edge snapped on the neck 18 of a release member 19 fitting over the outer end of the cartridge, the neck 18 of the release member 19 being so much shorter than the neck of the cartridge that it may be axially displaced along the neck of the cartridge limited by its outer end abutting the ferrule or by its shoulder abutting the shoulder of the cartridge.

The nozzle element and release member 19 are kept in their position with the neck 18 of the release member 19 abutting the ferrule 8 by a helical spring 20 surrounding the central part 14 of the nozzle element 13 abutting at its one end the ferrule 8 and at its other end a contact face between the central part 14 and the skirt 17 of the nozzle element 13. In this position the radial ducts 9 lie opposite the sealing 7 and the valve is closed. When the release member 19 is displaced in its axial direction to bring its internal shoulders in abutment with the outer shoulders of the cartridge, the radial ducts 9 are passed past the sealing 7 and into the valve chamber 5 and a communication between the liquid in the cartridge is established through the chamber 5, the radial ducts 9, the bore 10 and the clearance between the inner element 11 and the nozzle element 13 to the spray nozzle 12. This way the liquid in the cartridge will be sprayed out through the nozzle 12 when set under pressure as described below.

The pressure in the cartridge is provided by exerting upon a piston 21, which closes the end of the cartridge opposite the neck, a force trying to force this piston into the cartridge. A sealing element, which here is shown as an O-ring mounted in a circumferential groove in the piston, provides a sealing between the piston and the cartridge wall.

A piston rod 22 engaging the piston 21 protrudes through an anti rotary disc 23 mounted at the end of the first housing element 1 to make the piston rod irrotational in relation to this housing element.

This may be obtained by the disc, as shown in FIGS. 4 and 5 having spaced teeth 42 along its periphery fitting into a castellated end of the first housing element and by the piston rod having a non-circular profile fitting into a corresponding central opening in the disc. The piston rod is a mainly cylindric, threaded rod having diametrically opposite axial recesses 25 engaged by corresponding diametrically opposite projections 26 in the mainly circular opening of the anti-rotary disc.

The mainly cylindric piston rod 22 is threaded and is surrounded by a nut element 27 having at its end facing and abutting the anti-rotary disc a short internal thread 28, the rest of the inner surface of the nut element 27 being smooth fitting over the threaded piston rod to guide this rod in its axial movement. The nut element has at its threaded end external axial ribs 29 engaging internal axial grooves in the second housing element 2 making the nut element 27 irrotational, but axially displaceable in this housing element.

The grooves in the second housing element are each defined by pairs of spaced internal projections 30 in the second housing element. Together with the ribs 29 ending in a plate 41 at the end abutting the anti-rotary disc the projections 30 define a stop for the movement of the nut element as the plate 41 fits closely into the circular bore of the second housing element and consequently will abut the ends of the projections 30 when the nut element is displaced into the second housing element. Thereby the maximal loading of the device is limited.

When the piston rod 22 is rotated relatively to the nut element 27 in one direction by rotating the first housing element relatively to the second housing element the nut element is moved away from its abutment 31 on the anti-rotary disc 23 and is displaced further into the second housing element compressing a helical spring 32 abutting at its one end the nut element and at its other end a protrusion on the inner surface of the tubular second housing element. The compressed spring 32 will try to press the nut element back to abut the disc 23, and this force exerted on the nut member will be transmitted to the piston rod and the piston through the threads in the nut element on the piston rod, thereby setting the content of the cartridge under pressure. This pressure may be released by operating the valve to spray out the preselected dose of the medicine in the cartridge. During this spraying the piston is moved into the cartridge until the nut member abuts the disc 23 again.

At its end opposite the piston the piston rod is provided with a head 40 limiting the movement of the nut element along the piston rod to assure that a dose exceeding the remaining liquid in the cartridge may not be preset.

The engagement between the piston rod 22 and the piston 21 is performed as a snap lock. This way the piston 21 may be driven into the cartridge by the piston rod 22, the snap lock connection being flexible to permit the piston to follow marginal volume variations caused by temperature variations.

The loading of the device by turning the housing elements 1 and 2 in one direction relatively to each other may also be annulled by rotating the two housing elements in the opposite direction relatively to each other until the nut element is displaced to abut the disc again. The mutually abutting surfaces of the nut element and the disc 23 are provided with respective ramps to prevent further relative rotation in this direction when the nut member abuts the disc. This way it is prevented that a further relative rotation of the housing elements in this direction will cause the piston rod to be drawn out of engagement with the piston.

The end of the tubular nut element opposite the disc is provided with a knob 33 having an outer cylindric surface fitting guidingly into the bore of the tubular second housing element and an end surface flush with the end edge of the second housing element when the device is not loaded. When the device is loaded and the nut element is displaced away from the disc, the knob is protruding from the end of the second housing element giving a tactile and visible information of the status of the device, i.e. whether the device is loaded or not.

The spray nozzle element 13 is covered by a cap 34 when the device is not in use. This cap is provided with a clip 35, so that it can be carried in a pocket like a pencil. The cap 34 fits over the first housing element 1 and when fitted on is adjacent to and flush with the second housing element 2. The adjacent edges of the second housing element 2 and the cap 34 are provided with a projection 38 and a corresponding recess 39, respectively, the projection engaging the depression when the cap is fitted on.

The cap is provided with internal grooves 36 engaged by external ribs 37 on the first housing element 1. Thereby the cap can be used for rotating the first housing element 1 relatively to the second housing element 2 when the cap is appropriately axially displaced on the first housing element to bring the projection 38 out of engagement with the recess 39. The projection 39 is made as an arrow pointing on a scale on the cap, so that a dosing measured in units may be set by the turning of the two housing elements relatively to each other. The rotatable connection between the two housing elements is provided with a click mechanism providing a hearable and perceptible click at each two units set.

When the dose is set, the cap is removed from the device and the nozzle element is inserted in a nostril, and the release member 19 is pulled further over the first housing element to release the dose which is sprayed out through the nozzle at an angle of 0°–30°. After use the cap is again fitted over the first housing element in a rotary position making the projection 38 engage the depression 39.

The first housing element forming the cartridge is made of a transparent material allowing the position of the piston to be observed to decide how much liquid is left. For this purpose the first housing element may be provided with a scale. When the cartridge is empty, the device may be disposed of.

Although the device is described with the cartridge forming an integral part of the first housing element, an embodiment wherein a separate cartridge is received in the first housing element will be within the scope of the invention. The device may also be a durable one in which only the cartridge and possibly the valve and the spray nozzle are changed when the cartridge is empty, whereas the dose setting mechanism is reused as a durable part.

The device is preferably used for dosing insulin which may be assimilated through the nasal mucous membranes, but it is may also be used for the administration of other kinds of medicine which should be added as a spray in preset doses, e.g. for curing eczema.

We claim:

1. A device for nasal administration of a number of measured doses of a liquid, medicine, especially insulin, comprising a first and a second housing element and means coupling said housing elements together to allow rotation but no axial displacement of the first housing element (1) with respect to the second housing element (2), said first housing element (1) comprising a cartridge containing liquid medicine and being sealed by a piston (21) at a first end coupled to the second housing element (2) and being at its other end closed by a valve (7,9) to communicate the liquid medicine in the cartridge with a spray nozzle (12) upon opening of said valve characterized in that the device further comprises a threaded piston rod (22) engaging the piston (21) of the cartridge irrotational with respect to the first housing element (1) and disposed in the second housing element (2) to move axially therein, a nut element (27) mounted irrotational but axially displaceably in the second housing element (2) and engaging the thread of the piston rod (22), a helical spring (32) abutting at one end an internal annular abutment on the second housing element (2) and at its other end a shoulder on the nut element (27) to press the nut element and thereby the piston rod (22) and the piston (21) in the direction towards an outlet end of the cartridge to set the liquid medicine therein under pressure, means for spraying out a dose of the liquid medicine under pressure upon opening said valve, the housing elements (1,2), the piston rod (22), and the nut element (27) cooperating so that relative rotation between the housing elements (1,2) in a selected direction causes relative rotation between the rod (22) and the nut element, making the nut element move axially in the second housing element (2) in a direction to compress the helical spring (32).

2. A device according to claim 1, characterized in that the piston rod (22) is snap locked into the piston (21).

3. A device according to claim 1, characterized in that the nozzle (12) sprays out the liquid at an angle of 0°-30°.

4. A device according to claim 1, characterized in that the nut element (27) defines at least one radially protruding, axially extending projection (29) on an exterior portion thereof; and the projection is received in an axially extending groove in an inner portion of the second housing element (2).

5. A device according to claim 1, characterized in that a stop (30,41) is provided limiting axial movement of the nut element (27) into the second housing element (2).

6. A device according to claim 1, characterized in that a stop (40) is provided limiting the movement of the nut element (27) along the piston rod (22).

7. A device according to claim 1, further characterized in a removable protective cap (34) configured to receive the first housing element (1) and having abutting edges that abut corresponding abutting edges on the second housing element (2); and means (36,37) for releasably coupling the protective cap (34) and the first housing element (1) for rotation together, so that rotation of the protective cap (34) with respect to the second housing element (2) causes rotation of the first housing element (1) with respect to the second housing element (2).

8. A device according to claim 7, characterized in that the abutting edges of the second housing element (2) and the protective cap (34) comprise pointing means and scale means, respectively, for measuring the relative rotation of the protective cap (34) with respect to the second housing element (2).

9. A device according to claim 8, characterized in that means are provided for providing detents at selected rotational positions of the first housing element (1) with respect to the second housing element (2).

10. A device according to claim 9, characterized in that the coupling means (36,37) allow the protective cap (34) to receive the first housing element (1) in multiple different angular positions of the protective cap (34) with respect to the first housing element (1) to allow the protective cap (34) to be oriented at a selected position with respect to the second housing element (2), regardless of the detent rotational position of the first housing element (1) in the second housing element (2).

11. A device according to claim 10, characterized in that the interlocking means comprise a recess (38) on the abutting edges of the protective cap (34) and a projection (39) on the abutting edges of the second housing element (2), the projection (39) being shaped to fit into the recess (38) to define the selected position.

12. A device according to claim 9, characterized in that the abutting edges of the protective cap and the second housing element have interlocking means (38,39) for defining a selected angular position of the protective cap (34) with respect to the second housing element (2).

13. A device according to claim 1, characterized in that the piston rod (22) is made irrotational with respect to the first housing element (1) by fitting through an opening in an anti-rotation disc (23), the opening being mainly circular with at least one projection (26) protruding into the opening, by the piston rod (22) having a corresponding profile with recesses (25) corresponding to the projections (26), and by the anti-rotation disc (23) being at its periphery provided with alternating spaces and teeth (42) fitting into a castellated end of the first housing element (1).

14. A device according to claim 13, characterized in that the anti-rotation disc (23) serves as an abutment for the nut element (27) and limits movement of the nut element towards the cartridge.

15. A device according to claim 14, characterized in that the abutment between the nut element (27) and the anti-rotation disc (23) are formed as annular ramps (31) which when in mutual abutment allow only relative rotation of the first and second housing element in a device loading direction.

16. A device according to claim 15, characterized in that the nut element (27) has an tubular extension coaxially surrounding the piston rod (22) and terminated by a knob (33) at an outer end of the second housing element (2), the knob (33) being flush with the edge of the outer end of the second housing element when the annular ramps of the anti-rotation disc and the nut element are in mutual abutment.

* * * * *